(12) United States Patent
Nekovar et al.

(10) Patent No.: US 7,616,983 B2
(45) Date of Patent: Nov. 10, 2009

(54) DEVICE FOR GUIDING A MAGNETIC ELEMENT

(75) Inventors: Anton Nekovar, Neunkirchen (DE); Hans-Joachim Reich, Röttenbach (DE)

(73) Assignee: Siemens Aktiengesellschaft, Munich (DE)

( * ) Notice: Subject to any disclaimer, the term of this patent is extended or adjusted under 35 U.S.C. 154(b) by 477 days.

(21) Appl. No.: 11/230,802

(22) Filed: Sep. 20, 2005

(65) Prior Publication Data

US 2006/0062347 A1     Mar. 23, 2006

(30) Foreign Application Priority Data

Sep. 22, 2004    (DE) .................. 10 2004 045 989

(51) Int. Cl.
    *A61B 5/05*    (2006.01)
(52) U.S. Cl. .................. 600/427; 600/410; 600/407; 600/424; 600/429; 600/431; 378/196; 378/197; 378/198; 378/193; 335/306; 335/302; 335/296
(58) Field of Classification Search ............. 600/407, 600/410, 429, 431, 424, 426, 427; 378/193–198; 335/296, 302, 306
    See application file for complete search history.

(56) References Cited

U.S. PATENT DOCUMENTS

| 5,901,200 | A | 5/1999 | Krause | |
|---|---|---|---|---|
| 6,148,823 | A | 11/2000 | Hastings | |
| 6,241,671 | B1 | 6/2001 | Ritter et al. | |
| 6,755,816 | B2 | 6/2004 | Ritter et al. | |
| 6,975,197 | B2 * | 12/2005 | Creighton, IV | 335/306 |
| 7,246,943 | B2 * | 7/2007 | Gotoh | 378/196 |
| 2004/0252809 | A1 | 12/2004 | Kotian et al. | |
| 2005/0256398 | A1 * | 11/2005 | Hastings et al. | 600/423 |

FOREIGN PATENT DOCUMENTS

| DE | 42 24 614 A1 | 1/1994 |
|---|---|---|
| DE | 199 45 380 A1 | 3/2001 |
| DE | 103 56 325 A1 | 6/2004 |
| EP | 1 547 540 A1 | 6/2005 |
| WO | WO 03/077762 A1 | 9/2003 |

* cited by examiner

*Primary Examiner*—Brian Casler
*Assistant Examiner*—John F Ramirez

(57) ABSTRACT

A device for guiding a magnetic element has magnet holders that can be pivoted about vertical axes from an operating position to a rest position, such that a patient to be examined can be examined using imaging devices, having X-ray radiation sources and X-ray detectors respectively attached to C-arms.

3 Claims, 3 Drawing Sheets

DEVICE FOR GUIDING A MAGNETIC ELEMENT

CROSS REFERENCE TO RELATED APPLICATIONS

This application claims priority to the German application No. 10 2004 045 989.4, filed Sep. 22, 2004 which is incorporated by reference herein in its entirety.

FIELD OF INVENTION

The invention relates to a device for guiding a magnetic element in a body with at least one pair of guide magnets and with at least two imaging devices, having a radiation source and a radiation detector respectively.

BACKGROUND OF INVENTION

Such a device is known from U.S. Pat. No. 6,148,823. The known device has a yoke made of a magnetically soft material that is supported such that it can be pivoted and moved. Permanent magnets are arranged at the ends of the yoke. The magnetically soft yoke and permanent magnets can be moved to the head of a patient, to control a magnetic element, for example the magnetic tip of a catheter. Two imaging devices are provided to monitor the movement of the magnetic element, having a radiation source and a radiation detector respectively. The imaging devices are attached at right angles to each other on a C-arm that can be moved in a peripheral direction and can be pivoted about a radial axis.

If a magnetic element is to be moved inside the body of a patient, the magnetic yoke is moved such that the magnetic element is located in the gap between the permanent magnets of the magnetic yoke. The magnetic element is then moved away from the magnetic field between the permanent magnets of the magnetic yoke in the required direction by moving the magnetic yoke in an appropriate manner.

SUMMARY OF INVENTION

One disadvantage of the known device is that the design of the device has to be tailored in each instance to the examination of a specific part of the body. The known device is for example suitable for treating the head region of a patient. It is also not possible to examine the cardiac region, the abdominal area or the urogenital area with the known device.

An object of the invention is to create a device for guiding a magnetic element that can be used in a flexible manner.

This object is achieved by a device with the features of the independent claim. Advantageous embodiments and developments will emerge from the dependent claims.

The device has at least two imaging devices, having a radiation source and a radiation detector respectively. The radiation source assigned to an imaging device and the associated radiation detector are attached respectively to one end of an arm that can be pivoted about a radial axis and moved in a peripheral direction. The guide magnets and at least one of the imaging devices are also supported such that in the event of a collision the guide magnets or the imaging device can be moved out of a common operating area.

Because each imaging device is assigned a separate arm that can be pivoted about a radial axis and moved in a peripheral direction, the positions of the imaging device are mutually independent. The two imaging devices can be positioned in a flexible manner during the treatment of a patient. If it is also necessary to continue the treatment or examination of the patient using a magnetic field, at least one of the imaging devices can be moved out of the operating area of the guide magnets, such that the operating area common to the guide magnets and the imaging device is available to the guide magnets alone. Conversely the guide magnets can also be moved out of the common operating area so that the imaging device can be moved freely.

In one embodiment the guide magnets are attached to supports that are arranged on opposite sides of a patient bed. The guide magnets can also be pivoted about at least two axes perpendicular to a longitudinal axis of the guide magnet device, such that magnetic fields with different directions and different gradients can be established in the space between the guide magnets. As the guide magnets are located to the side of the patient bed, the guide magnets can essentially be moved to any position along the longitudinal axis of the patient bed. This means that almost any area of the body of a patient can be examined.

In a further embodiment the guide magnets are attached to a floor-mounted support, each of which can be pivoted about a vertical axis. This means that the entire device is relatively compact, as the rest position of the guide magnets does not require an unnecessarily large amount of space.

The ends of the supports of the guide magnets facing away from the patient bed are preferably supported such that they can be rotated about an axis of rotation and the ends of the supports facing the patient bed preferably rest on semi-circular rails. Such a support allows even heavy guide magnets to be held and moved without a great deal of force.

As the supports the for guide magnets are generally not mounted such that they can be moved longitudinally along the patient bed, the patient bed is preferably supported such that it can be displaced longitudinally, such that different regions of the body can be moved into the space between the guide magnets.

There is also provision for one of the arms supporting the imaging device to be attached to the ceiling in a movable manner. Such an arm can be moved in a simple manner out of the operating area of the guide magnets, without having to take into account objects on the floor.

A further floor-mounted arm can also be provided that can be moved from a position centered on the longitudinal axis of the patient bed to a position away from the longitudinal axis of the patient bed. This allows the patient bed to be moved past the support for the floor-mounted arm, so that it is also possible to examine the abdominal or urogenital area of a patient.

BRIEF DESCRIPTION OF THE DRAWING

Further details and advantages of the invention will emerge from the description which follows, in which exemplary embodiments of the invention are described in detail with reference to the drawing, in which.

DETAILED DESCRIPTION OF INVENTION

Figure 1:
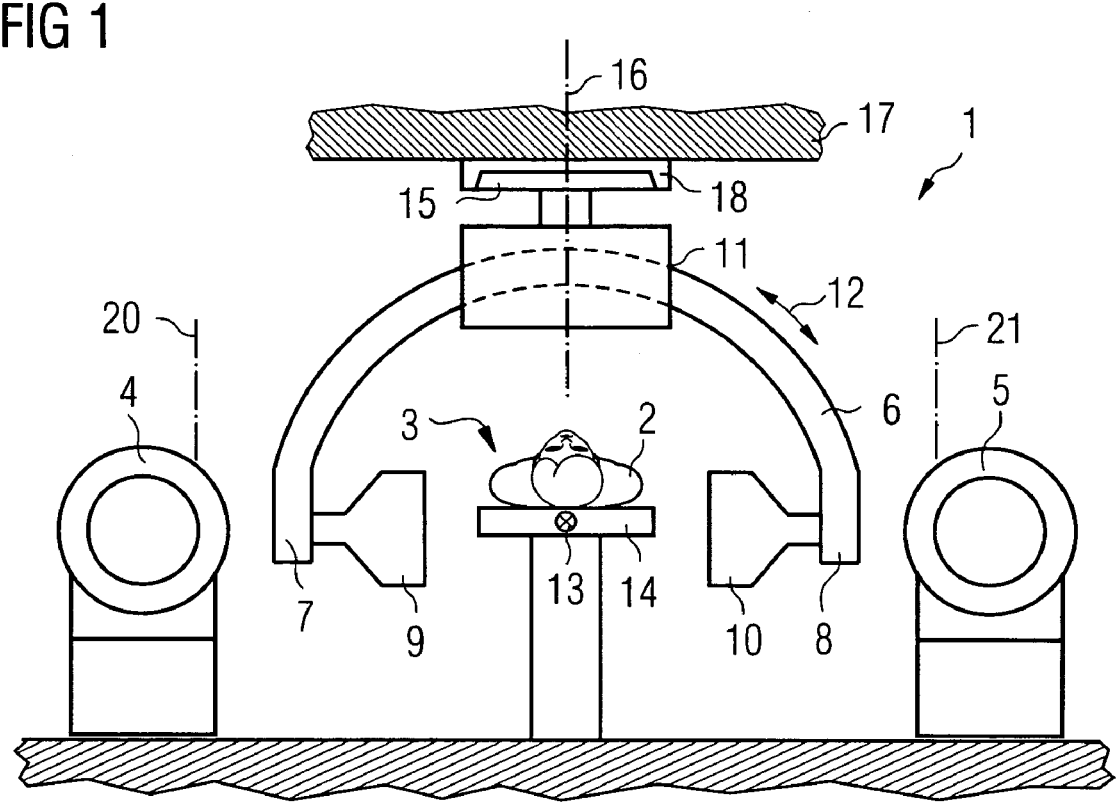
FIG. 1 shows a front view of a device for guiding a magnetic element, without a floor-mounted arm.

FIG. 1 shows a view of the device 1, which serves to guide a magnetic element, for example the magnetic tip of a catheter, in the body 2 of a patient 3. To this end the device 1 has magnet holders 4 and 5. Guide magnets are located inside the housings of the magnet holders 4 and 5. The guide magnets may be permanent magnets or electromagnetic magnets.

The device also has a C-arm 6, at the ends 7 and 8 of which an X-ray radiation source 9 and an X-ray detector 10 respectively are attached. The C-arm 6 is supported in the support 11 such that the C-arm 6 can be moved in a peripheral direction 12. The X-ray radiation source 9 and the X-ray detector 10 thereby rotate about an isocenter 13 about a patient bed 14, on which the patient 3 is lying.

The support 11 is attached to a carriage 15. The support 11 is thereby supported such that the support 11 can be rotated together with the C-arm 6 about an axis of rotation 16. During one rotation about the axis of rotation 16 the X-ray radiation source 9 and the X-ray detector 10 rotate about the isocenter 13. The carriage 15 can also be moved along a track 18 mounted on the ceiling 17.

The magnet holders 4 and 5 can also be moved. Because the magnet holders 4 and 5 are heavy, the magnet holders 4 and 5 are attached to a base 19 and can be pivoted about axes of rotation 20 and 21 to bring them close to the patient bed 14.

Figure 2:
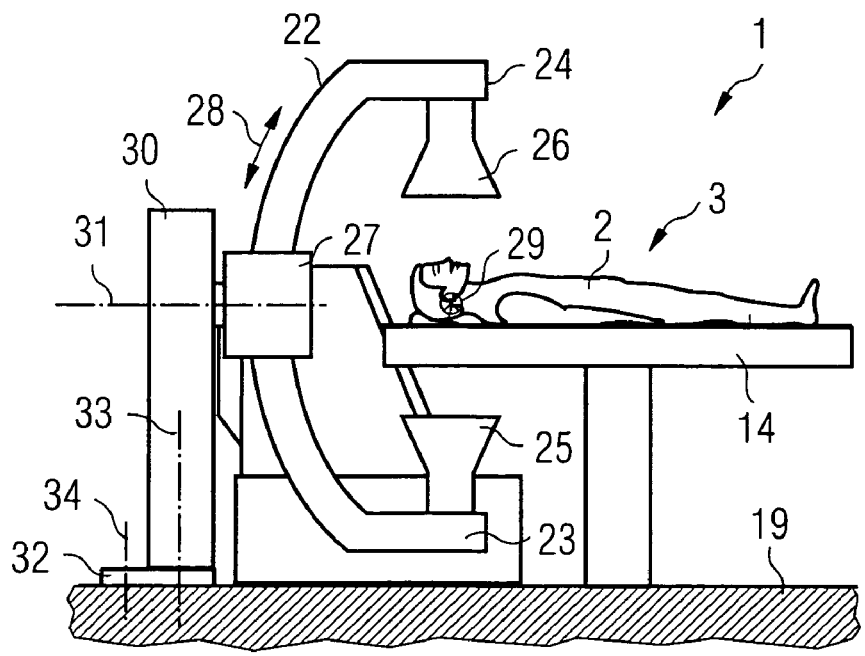
FIG. 2 shows a side view of the device from FIG. 1, without a ceiling-mounted arm.

FIG. 2 shows a further element of the device 1, namely a C-arm 22 mounted on the floor 19. The C-arm 22 has an X-ray radiation source 25 and an X-ray detector 26 respectively at its ends 23 and 24.

The C-arm 22 is supported in the support 27 such that the C-arm 22 can be moved in a peripheral direction 28. The X-ray radiation source 25 and the X-ray detector 26 thereby execute a rotational movement about an isocenter 29.

The support 27 is attached to a stand 30, such that the support 27 can be rotated about an axis of rotation 31 together with the C-arm 22. The X-ray radiation source 25 and the X-ray detector 26 thereby execute a rotational movement about the isocenter 29. The stand 30 is also supported on a base plate 32 such that it can be rotated about an axis of rotation 34. The base plate 32 is in turn attached to the floor 19 such that it can be rotated about an axis of rotation 34.

Figure 3:
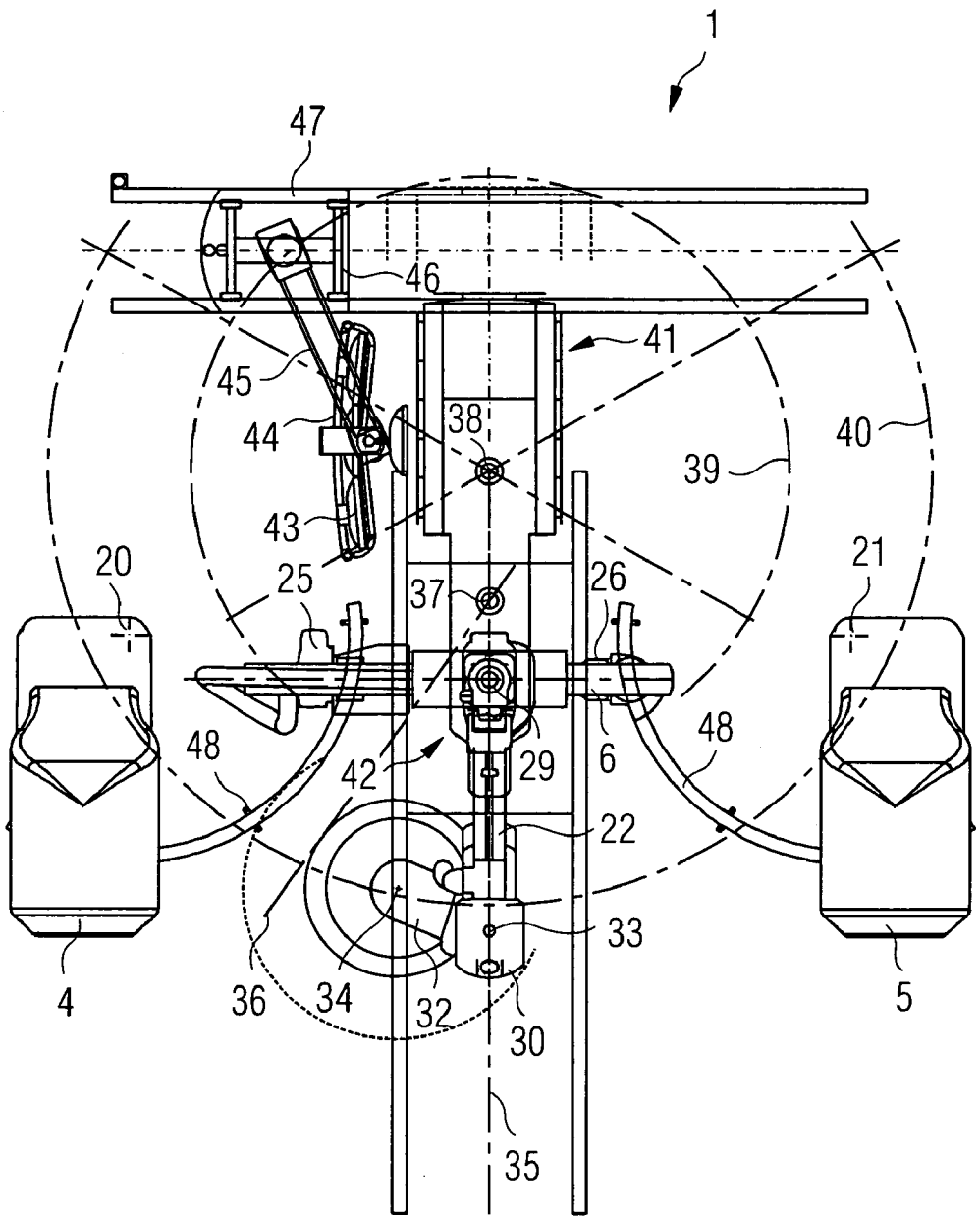
FIG. 3 shows a plan view of the device from FIGS. 1 and 2 with the guide magnets in the park position.
Figure 4:
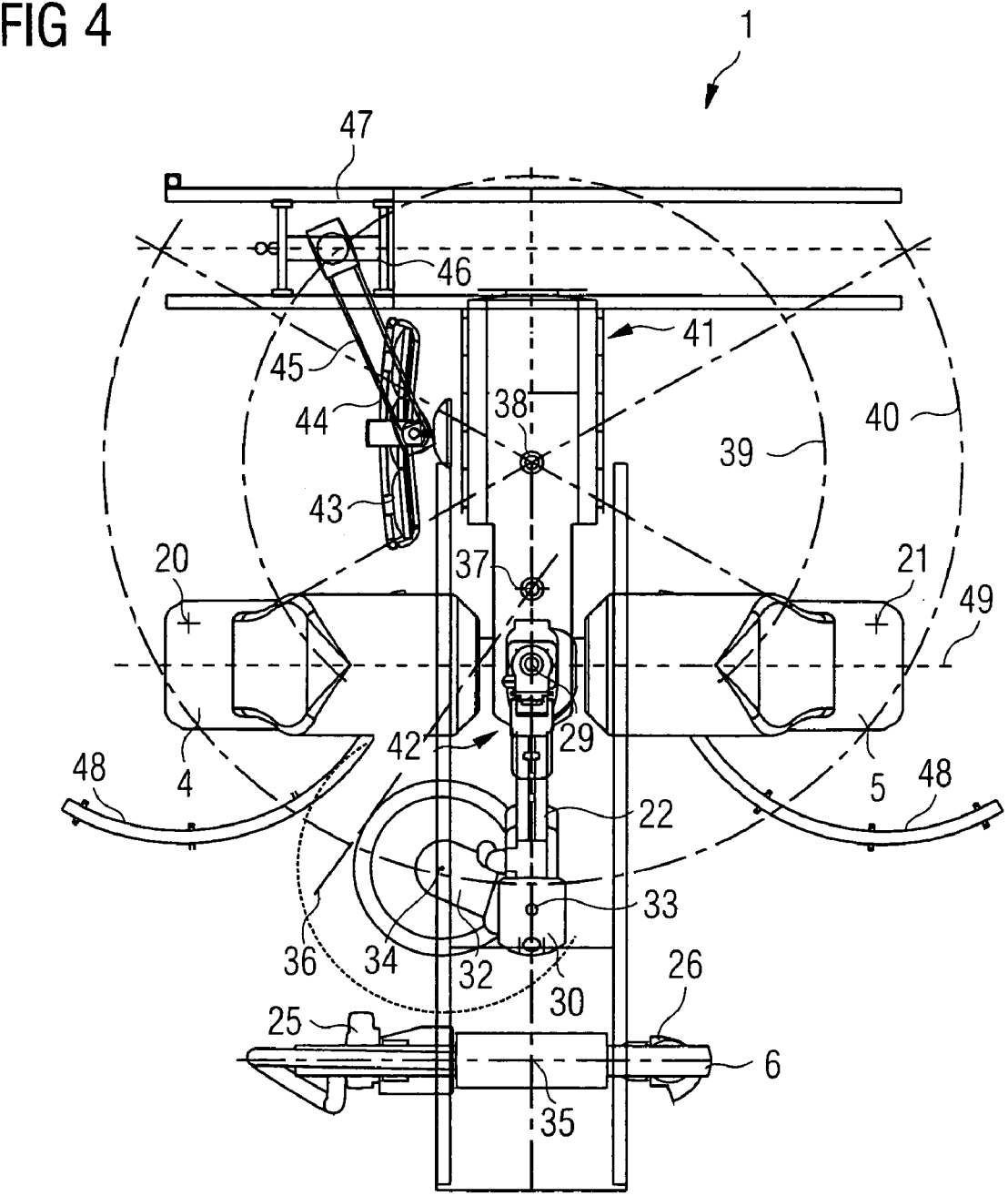
FIG. 4 shows a plan view of the device from FIGS. 1 and 2 with the guide magnets in the operating position.

FIGS. 3 and 4 show plan views of the device 1 in different operating states.

FIG. 3 shows the magnet holders 4 and 5 in a park position. The ceiling-mounted C-arm 6 is in the operating position in proximity to the patient bed 14. In the situation shown in FIG. 3 the isocenters 13 and 29 in particular are superimposed. The two C-arms 6 and 22 can be used to examine the patient 3 thoroughly using the X-ray radiation sources 9 and 25 and the X-ray detectors 10 and 26.

In this operating state it is also possible to move the stand 30 into a position away from a longitudinal axis 35 by rotating the base plate 32 about the axis of rotation 34. The alignment that the C-arm 22 then assumes is shown in FIG. 3 by an axis 36. The isocenter 29 then moves to a point of intersection 37 of the axis 36 and the longitudinal axis 35.

As the patient bed 14 can not only be moved along the longitudinal axis 35 but can also be pivoted about an axis of rotation 38, outlines 39 and 40 are marked in FIG. 3 to show the areas covered by the patient bed 14 during rotation about the axis of rotation 38. The outline 39 thereby shows the area covered by the foot end 41 of the patient bed 14 with maximum displacement of said patient bed 14, while the outline 40 shows the area covered by a head end 42 of the patient bed 14 with maximum displacement of said patient bed 14.

For the sake of completeness, monitors 43 are also shown in FIGS. 3 and 4, on which the doctor providing the treatment can view the images recorded by the X-ray detectors 10 and 26. The monitors 43 are located in a support 44, suspended from an arm 45. The arm 45 is attached to a trolley 46 that runs on ceiling-mounted rails 47.

FIG. 4 shows a further plan view of the device 1, in which the magnet holders 4 and 5 are moved into the operating position by rotation about the axes of rotation 20 and 21. During rotation about the axes of rotation 20 and 21 the magnet holders 4 and 5 run on rails 48 that are preferably let into the floor.

While the magnet holders 4 and 5 are moved into the operating position, the ceiling-mounted C-arm 6 is moved to a rest position.

In the operating state shown in FIG. 4 the X-ray radiation source 25 and the X-ray detector 26 as well as the guide magnets arranged in the magnet holders 4 and 5 can be used to navigate a magnetic element in the body 2 of the patient 3 through the body 2 of the patient 3.

In the operating position shown in FIG. 4 the magnet holders 4 and 5 are aligned on a common longitudinal axis 49. The guide magnets inside the magnet holders 4 and 5, which are preferably in the form of permanent magnets, can be pivoted perpendicular to the longitudinal axis 49. The guide magnets can generally be pivoted about two axes of rotation running perpendicular to the longitudinal axis 49.

The device 1 described in the said FIGS. 1 to 4 has a high level of flexibility. Different types of examination and treatment can be carried out on the body 2 of a patient 3 without having to move said patient 3 to a different bed and without obstructing the individual elements of the device 1. The doctor providing the treatment therefore has a twin-level X-ray fluoroscopy system available to them. It is possible if necessary to switch to magnetic navigation using the magnet holders 4 and 5 without having to move the patient 3 to a different bed. If the doctor finds it necessary to find their way using a twin-level fluoroscopy system, this can once again be used by moving the magnet holders 4 and 5 out of the common operating area with the C-arm 6 and moving the C-arm 6 into the common operating area.

The invention claimed is:

1. A device for guiding a magnetic element in a body to be examined in an operating area, the device comprising:
   a support device for a body to be examined comprising a bed, said bed configured to be displaced longitudinally such that the bed can be moved longitudinally along an operating area allowing different regions of the body to be moved longitudinally into and out of the operating area;
   at least one pair of guide magnets used to navigate a magnetic element in the body, said guide magnets disposed within a pair of floor-mounted magnet holders on opposite sides of the bed, each magnet holder fixed about a pivot point on a semi-circular rail support, to allow independent pivoting about a vertical axis at the pivot point and each magnet holder configured to be independently pivoted into the operating area on the semi-circular rail support so that the magnet holders have a common longitudinal axis and to be pivoted out of the operating area on the semi-circular rail support, wherein the semi-circular rail support allows the magnet holders to be moved without a great deal of force into and out of the operating area without a longitudinal movement of the magnet holders;
   two C-shaped arms comprising imaging devices having a radiation source and a radiation detector arranged at opposite ends of each C-shaped arm; wherein each C-shaped arm is configured to be pivoted about a radial axis of the arm and to be moved in a peripheral direction relative to a circle around the radial axis, mutually independent of the other C-shaped arm;

wherein a first floor-mounted C-shaped arm is mounted on a floor support at the head end of the bed; and wherein a second ceiling mounted C-shaped arm is mounted on a ceiling support above the operating area and configured to be moved longitudinally along the ceiling out of the operating area into a rest position when the magnet holders are pivoted into the operating area and configured to be moved longitudinally along the ceiling into the operating area when the magnet holders are pivoted out of the operating area into a park position.

2. The device according to claim 1, wherein the guide magnets are held in the magnet holders and configured to be pivoted along with the magnet holders into an operating position perpendicular to a longitudinal axis common to both guide magnets.

3. The device according to claim 1, wherein the floor-mounted C-shaped arm is configured to be moved into a position away from a longitudinal axis of the bed by pivoting the floor support, thereby allowing the bed to be moved passed the floor-mounted C-shaped arm to examine an abdominal or urogenital area of the body.

* * * * *

UNITED STATES PATENT AND TRADEMARK OFFICE
CERTIFICATE OF CORRECTION

PATENT NO. : 7,616,983 B2
APPLICATION NO. : 11/230802
DATED : November 10, 2009
INVENTOR(S) : Nekovar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 683 days.

Signed and Sealed this

Nineteenth Day of October, 2010

David J. Kappos
*Director of the United States Patent and Trademark Office*